United States Patent
Kankan et al.

(10) Patent No.: US 8,288,561 B2
(45) Date of Patent: Oct. 16, 2012

(54) PROCESS FOR PREPARING VALSARTAN

(75) Inventors: Rajendra Narayanrao Kankan, Maharashtra (IN); Dharmaraj Ramachandra Rao, Maharashtra (IN); Srinivas Laxminarayan Pathi, Karnataka (IN); Ravikumar Puppala, Karnataka (IN)

(73) Assignee: CIPLA Limited, Mumbai (IN)

( * ) Notice: Subject to any disclaimer, the term of this patent is extended or adjusted under 35 U.S.C. 154(b) by 0 days.

(21) Appl. No.: 12/598,791

(22) PCT Filed: May 7, 2008

(86) PCT No.: PCT/GB2008/001568
§ 371 (c)(1),
(2), (4) Date: Feb. 17, 2010

(87) PCT Pub. No.: WO2008/135762
PCT Pub. Date: Nov. 13, 2008

(65) Prior Publication Data
US 2011/0105763 A1    May 5, 2011

(30) Foreign Application Priority Data
May 7, 2007  (IN) .......................... 867/MUM/2007

(51) Int. Cl.
*C07D 257/00* (2006.01)
*C07D 257/04* (2006.01)

(52) U.S. Cl. ....................................... 548/253; 548/255

(58) Field of Classification Search ................... 548/255
See application file for complete search history.

(56) References Cited

U.S. PATENT DOCUMENTS

| | | | |
|---|---|---|---|
| 5,399,578 A * | 3/1995 | Buhlmayer et al. | 514/381 |
| 5,965,592 A * | 10/1999 | Buhlmayer et al. | 514/381 |
| 7,199,144 B2 | 4/2007 | Rukhman et al. | |
| 2005/0059827 A1 * | 3/2005 | Rukhman et al. | 548/254 |
| 2006/0281801 A1 | 12/2006 | Kumar et al. | |

FOREIGN PATENT DOCUMENTS

| | | |
|---|---|---|
| EP | 1661891 A1 | 5/2006 |
| IN | 421/CHENP/2005 | 4/2007 |
| WO | 2004101534 A1 | 11/2004 |
| WO | 2007032019 A2 | 3/2007 |
| WO | 2008004110 A2 | 1/2008 |
| WO | 2008135762 A1 | 11/2008 |

OTHER PUBLICATIONS

Stahl et al., eds., Handbook of pharmaceutical salts. Properties, selection and use (Wiley-VCH, 2008), pp. 265-327.*
Foreign communication from the priority application—International Preliminary Report on Patentability, PCT/GB2008/001568, Nov. 10, 2009, 6 pages.
Foreign communication from the priority application—International Search Report and Written Opinion, PCT/GB2008/001568, Oct. 6, 2008, 13 pages.
Narayan, Bhanu Manjunath, et al., "An improved process for the synthesis of valsartan of high enantiomeric purity," Jun. 8, 2007, Chemical Abstracts Service, XP002496724.
Paquette, L.A., "Encyclopedia of Reagents for Organic Synthesis," Encyclopedia of Reagents for Organic Synthesis, vol. 6, Jan. 1, 1995, pp. 3812-3814, XP002464887.
Riemenschneider, W., "Oxalic Acid, 9. Derivatives," Ullmann's Encyclopedia of Industrial Chemistry, vol. 24, Jan. 1, 2003, p. 483, XP002464886.

* cited by examiner

*Primary Examiner* — Susannah Chung
(74) *Attorney, Agent, or Firm* — Conley Rose, P.C.; Rodney B. Carroll

(57) ABSTRACT

An N-[(2'-(1-triphenyl methyl tetrazole-5-yl)biphenyl]-4-yl] methyl]-L-valine benzyl ester organic salt of formula (IVA) wherein A represents an organic carboxylic acid, a process for its preparation and its use in the synthesis of valsartan or salts thereof.

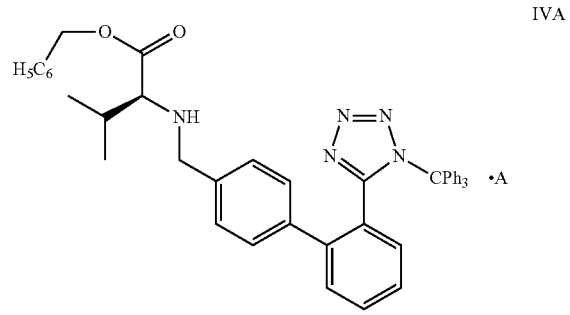

11 Claims, No Drawings

PROCESS FOR PREPARING VALSARTAN

FIELD OF THE INVENTION

The invention relates to a novel process for the preparation of valsartan.

BACKGROUND OF THE INVENTION

Valsartan is a commonly-available specific angiotensin II antagonist which acts on the $AT_1$ receptor subtype. It is used in the treatment of hypertension, diabetes related hypertension, heart attack, post myocardial infarction and lung cancer. The structure of valsartan is as shown below:

Formula (I):

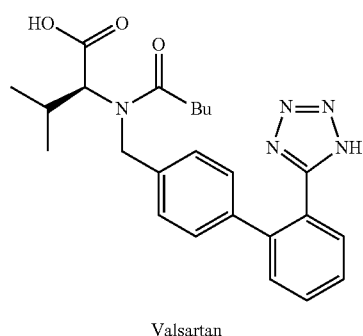

Valsartan

Chemically, valsartan is known as N-(1-oxopentyl)-N-[[2'-(1H-tetrazol-5-yl)-[1,1'-biphenyl]-4-yl]methyl]-L-valine, has a molecular weight of 435.5 and the chemical formula $C_{24}H_{29}N_5O_3$. Valsartan is a white to practically white fine powder. It is soluble in ethanol, methanol and is slightly soluble in water.

Biologically, valsartan is a non-peptide and is capable of oral administration. Tablets of the compound with strength 40 mg, 80 mg, 160 mg and 320 mg are available.

Valsartan was first disclosed in U.S. Pat. No. 5,399,578, hereinafter referred to as '578. The patent describes a procedure for the preparation of valsartan as depicted in Scheme 1.

Scheme 1

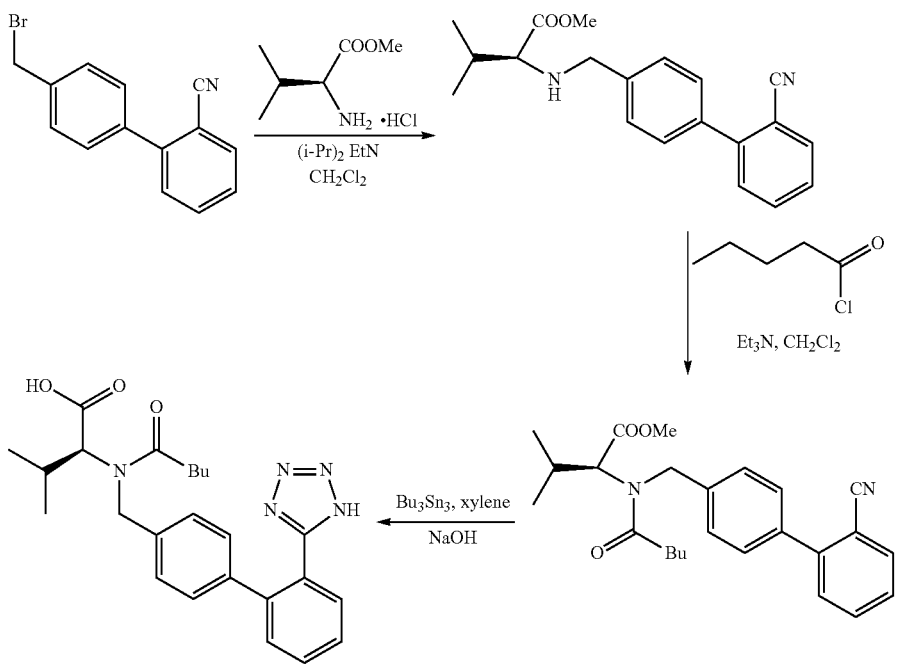

The process disclosed in the scheme 1 has the following disadvantages.

a) The unavoidable use of toxic tributyl azide in the formation of the tetrazole ring. Reaction in the presence of tributyl azide leads to the formation of hydrogen azide which is explosive in nature. Moreover, tributyl azide is a hazardous chemical in itself. Use of the same on an industrial scale necessitates professional handling at all times. This leads to an overall increase in the handling and production costs.

b) The intermediates formed in the disclosed Scheme I are oily in nature. Their crystallization is an enormous task which often requires repeated steps of crystallization. The yield and the quality of the end product obtained by using the stated procedure in accordance with Scheme I is therefore greatly compromised. Moreover the crystallizations and re-crystallizations procedures carried out on an industrial scale, make the process laborious and time consuming.

The '578 patent discloses an alternate process for the preparation of valsartan, wherein 4-bromomethyl-2'-(1-triphenylmethyltetrazol-5-yl)biphenyl is reacted with (L)-valine benzyl ester hydrochloride in DMF to obtain N-[(2'-tetrazolylbiphenyl-4-yl)methyl]-(L)-valine benzyl ester. This is then acylated with valeryl chloride. The benzyl ester group is then removed by hydrogenation to obtain valsartan. The reaction procedure is depicted in Scheme 2.

Scheme 2:

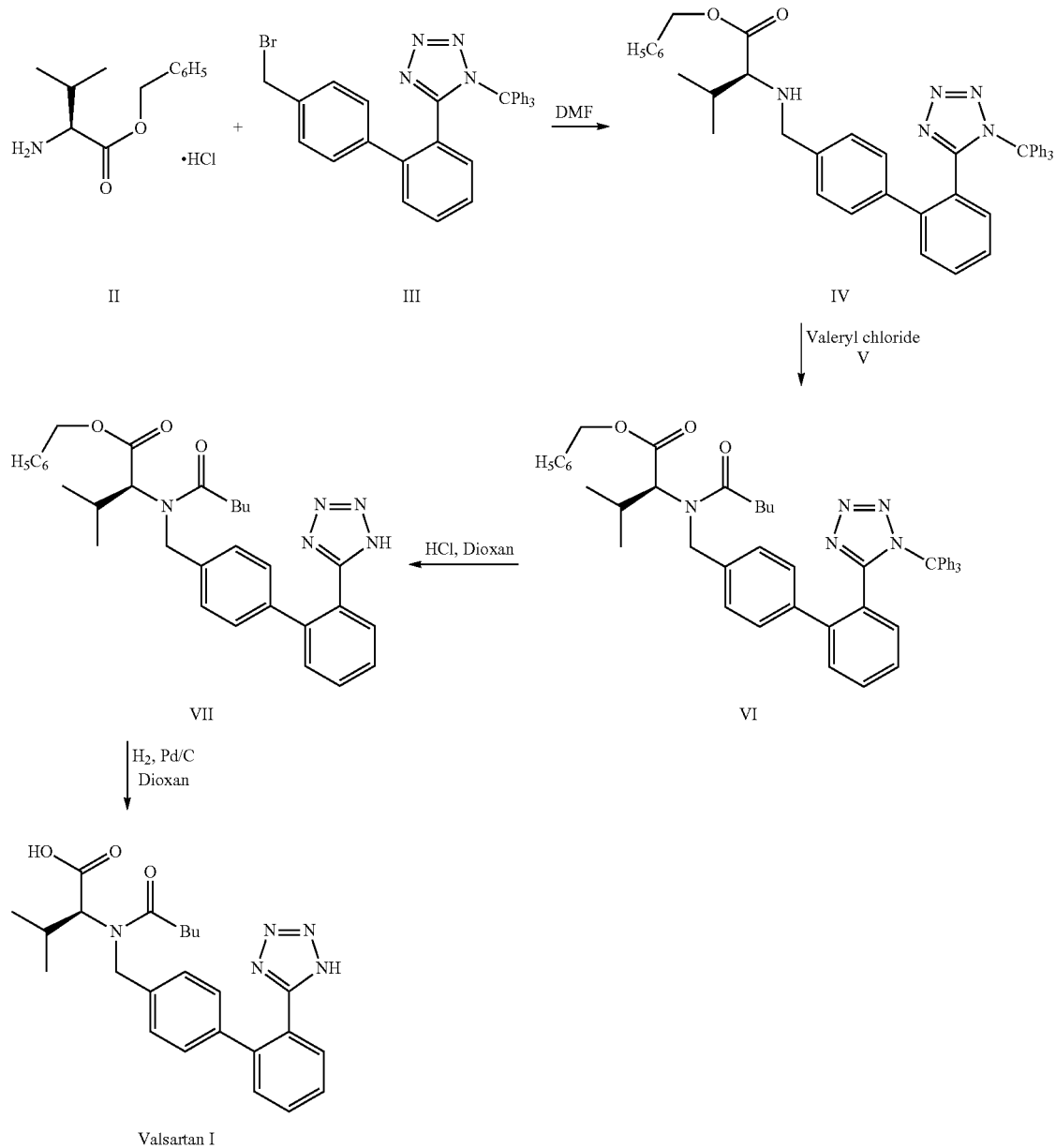

A disadvantage of the process according to Scheme 2 is that all intermediates obtained are oily in nature and their crystallization from this oily form is very difficult. This in turn affects both the yield and purity of the final product. Re-crystallization procedures become mandatory for the improvement of the yield. These are necessarily time consuming and further add to the net cost of the product. The purity of the end product is greatly compromised owing to the presence of un-crystallized intermediates.

The other disadvantage of the '578 patent is that, one can not reproduce the result by following the processes as disclosed in Example 55. The procedure is limited to the method of preparation of benzyl ester only. Further, lack of data on weighed quantities of the reactants and incomplete disclosure of synthesis steps limit the scope of the patent's teachings for the preparation of valsartan. By following the analogous examples, valsartan was obtained with poor purity and had to be re-crystallized several times to achieve the desired purity. Many intermediates are isolated by flash chromatography. This requires an increased usage of raw materials, solvents, labor, energy and time. Eventually it adds to the net cost of the end product.

WO 2004/101534 (hereinafter referred to as '1534) focuses on a process for the preparation of a valsartan where an intermediate of formula (IV) is converted to its hydrochloride salt as shown in Scheme 3.

Scheme 3

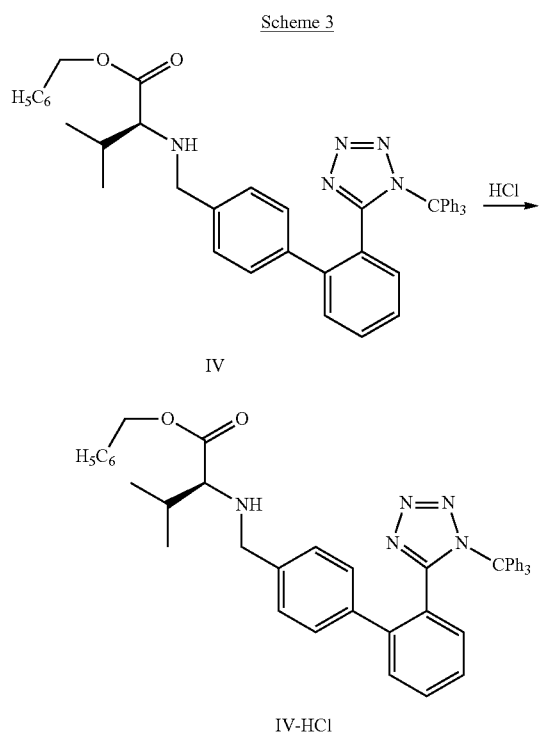

The hydrochloride salt is then converted to valsartan (I) by reacting with valeryl chloride (V) and removing protective groups.

The process according to Scheme 3 has the following disadvantages.

a) The preparation of the hydrochloride salt must be carried out at exact pH and temperature conditions only. Even a slight temperature rise or variation in pH leads to the detritylation of the intermediate resulting in undesired impurities. The purity of the final product is thus always a difficult consideration during the formation of the hydrochloride salt of this intermediate.

b) It is a known fact that, the trityl group is highly unstable in an acidic environment. Patent application '1534 teaches that the reaction must be carried out at a highly acidic pH of 1, to convert the intermediate IV into its hydrochloride salt. There are strong chances that detritylation of the protecting trityl group may occur at such adverse pH conditions. In case such detritylation does occur, the final yield of valsartan is inadvertently reduced. Thus, in effect, a process step which is introduced to ease the crystallization procedure may de-protect a desired group in the intermediate compound affecting the net purity. Also the possibility of production of some new intermediates owing to the occurrence of detritylation cannot be avoided. This may in turn result in undesired side reactions in the subsequent steps.

c) The hydrochloride salt (IV—HCl) is further purified using inflammable and hazardous solvents like hexane and has a purity of 92% only.

Indian application no 421/CHENP/2005 (herein after referred to as IN '421) discloses another process for preparation of valsartan and an intermediate IIa thereof. The process according to IN '421 does not use an azide moiety for the formation of tetrazole compound. The process according to the IN '421 application is shown in Scheme 4.

Scheme 4

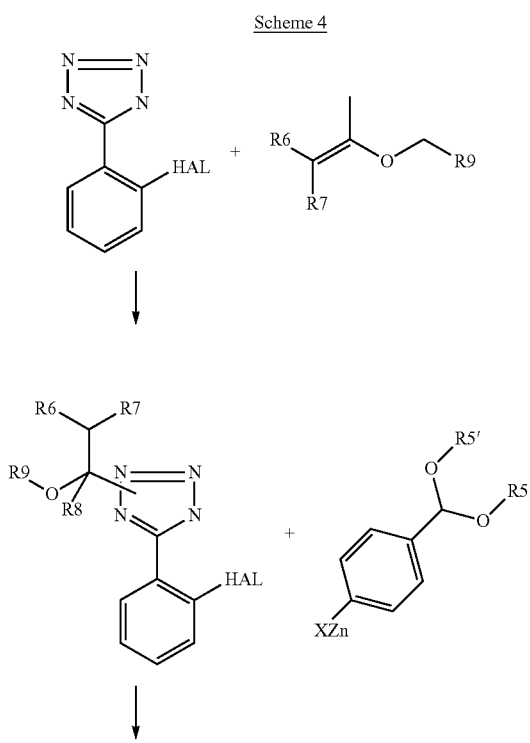

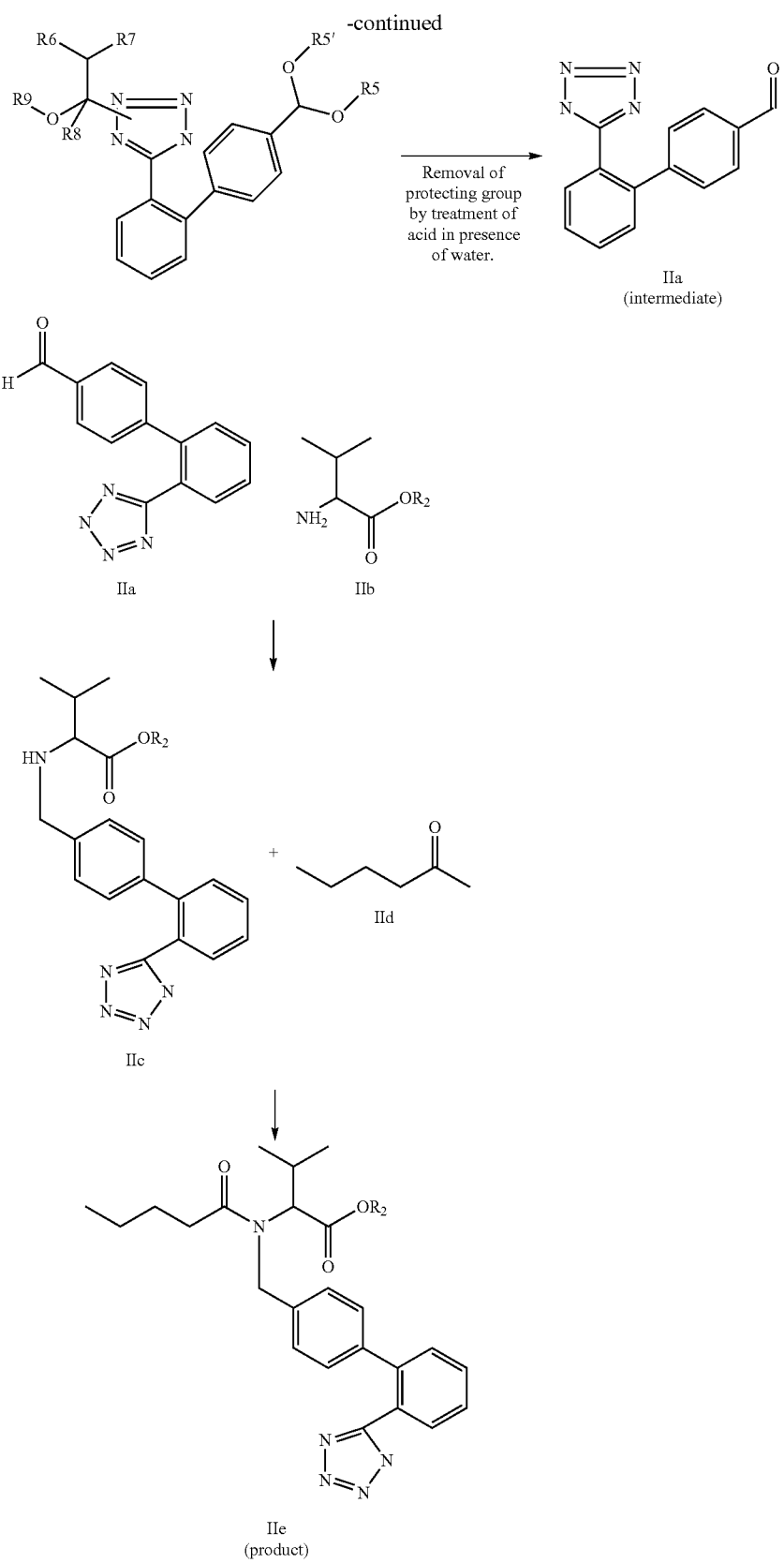
A disadvantage of the above process is that it requires strict maintenance of pH and the process is quite lengthy.
U.S. Pat. No. 7,199,144 (US '144) discloses yet another process for the preparation of valsartan and precursors thereof. The method of preparation of valsartan is the same as disclosed in '578, but it provides alternative methods to remove residual solvent, particularly ethyl acetate (of which the permissible limit is less than 5000 ppm) from the final product. The following methods used:

1) Crude, valsartan is triturated with water (about 4 liter/kg of crude product) at a temperature of around 24-40 degrees.
2) By performing a solvent exchange by contacting the solvate with humid gas in a fluidized bed apparatus at around 30 degrees.
3) By harsh drying which is carried out by maintaining the valsartan at a temperature of about 5 to about 60 degree C. under pressure of less than about 30 mmHg.

However, the disadvantages associated with the '578 patent, remain with the US '144 process, for example production of oily intermediates, unavoidable use of toxic azides and the like.

US 20060281801 discloses yet another process for the preparation of valsartan. It provides a purification method for the removal of the organotin impurity from benzyl valsartan. The purification process includes:

(1) Crystallization of benzyl valsartan from a ternary solvent mixture comprising a hydrophilic organic solvent, a non-polar organic solvent, and water
(2) Crystallization from a polar aprotic solvent, a non-polar organic solvent, or mixtures thereof. Preferably, the second crystallization solvent is a binary solvent mixture comprising a polar aprotic solvent and a non-polar organic solvent.

As the process requires a method for recrystallization, it is very time consuming and the purity of the end product is highly questionable as the intermediates are oily.

The processes disclosed in the prior art are therefore cumbersome and not feasible industrially.

Hence, there is a need to develop a more efficient and economical synthetic route suitable for industrial scale-up.

OBJECTS OF THE INVENTION

The object of the present invention is to provide an improved process for the preparation of valsartan (I) or pharmaceutically acceptable salts thereof.

Another object of the present invention is to provide a novel organic salt of N-[(2'-(1-triphenyl methyl tetrazole-5-yl)biphenyl]-4-yl]methyl]-L-valine benzyl ester of formula, (IVA) which is suitable for the synthesis of valsartan (I).

In another object, the present invention provides a process for the synthesis of the valsartan intermediate N-[(2'-(1-triphenyl methyl tetrazole-5-yl)biphenyl]-4-yl]methyl]-L-valine benzyl ester as an oxalate salt of formula (IVB).

Yet another object of the present invention is to provide a process for the preparation of valsartan compositions and formulations by using the valsartan produced by the present invention.

Yet another object is to provide a process which is simple, economical and suitable for industrial scale up.

SUMMARY OF THE INVENTION

According to a first aspect of the present invention, there is provided an N-[(2'-(1-triphenyl methyl tetrazole-5-yl)biphenyl]-4-yl]methyl]-L-valine benzyl ester organic salt of formula (IVA)

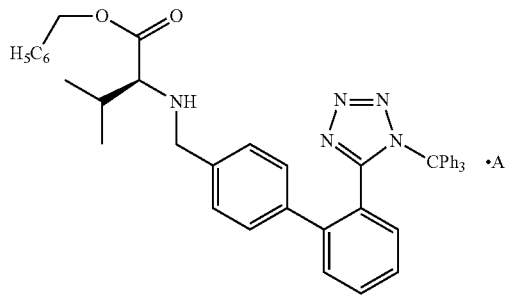

wherein A represents an organic carboxylic acid.

The term "organic salt" of a compound means the reaction product of the compound with an organic carboxylic acid.

In an embodiment, the organic acid is oxalic acid, acetic acid, formic acid, malic acid, maleic acid, malonic acid, succinic acid, fumaric acid, phthalic acid, terephthalic acid, citric acid, tartaric acid, methane sulfonic acid, ethane sulfonic acid, p-toluene sulfonic acid, trifluoroacetic acid or ascorbic acid. Preferably, A is oxalic acid.

According to another aspect of the present invention, there is provided a process for preparing a compound of formula (IVA)

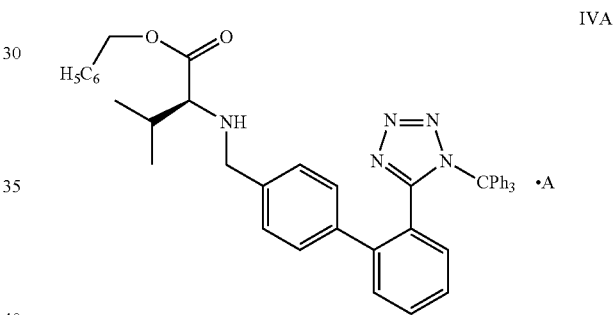

wherein A represents an organic carboxylic acid, which comprises reacting N-[(2'-(1-triphenyl methyl tetrazole-5-yl)biphenyl]-4-yl]methyl]-L-valine benzyl ester of formula (IV) with an organic carboxylic acid to obtain the compound of formula (IVA).

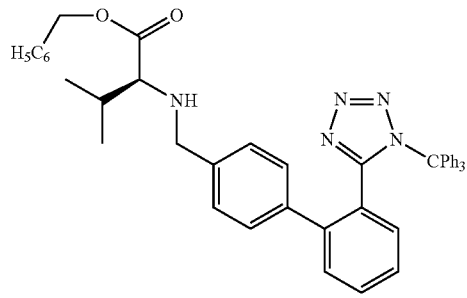

In an embodiment, the organic acid is oxalic acid, acetic acid, formic acid, malic acid, maleic acid, malonic acid, succinic acid, fumaric acid, phthalic acid, terephthalic acid, citric acid, tartaric acid, methane sulfonic acid, ethane sulfonic acid, p-toluene sulfonic acid, trifluoroacetic acid or ascorbic acid. Preferably, A is oxalic acid.

A solvent may be used in the step of converting IV to IVA, for example the solvent may be selected from the group consisting of water, methanol, ethanol, propanol, isopropanol, tert-butanol, ethyl acetate, acetone, toluene, n-hexane, o-xylene, n-heptane, methylenedichloride, ethylenedichloride, acetonitrile, dimethylformamide, dimethylsulfoxide or mixtures thereof, more preferably water, acetone, toluene, o-xylene or mixtures thereof.

In an embodiment, the compound of formula IV is prepared by reacting L-valine benzyl ester of formula (II)

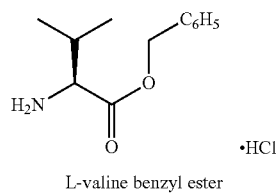

L-valine benzyl ester with 4-(bromomethyl-biphenyl-3-yl)-1-(triphenyl methyl) tetrazole of formula (III)

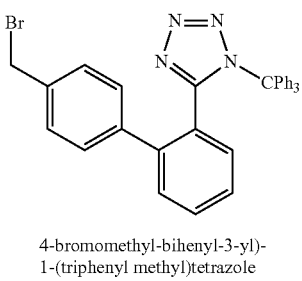

4-bromomethyl-bihenyl-3-yl)-1-(triphenyl methyl)tetrazole to obtain the compound of formula (IV). The reaction of compounds II and III may be carried out in the presence of a base, for example an alkali metal carbonate, such as potassium carbonate.

A solvent may be used in the step of reacting II and III, for example the solvent may be selected from the group consisting of dimethylformamide, dimethyl acetamide, dimethylsulfoxide, acetonitrile, xylene, toluene, a halogenated hydrocarbon such as methylenedichloride, ethylenedichloride or chloroform, an alcohol such as methanol, ethanol, n-propanol, isopropanol, n-butanol, isobutanol, tert-butanol, n-Amyl alcohol, isoamyl alcohol or tert-amyl alcohol or mixtures thereof. In one embodiment, the solvent used is acetonitrile.

The organic salts of formula IVA may be isolated from the reaction mass. The isolation be carried out in the absence of hexane. The organic salts of formula IVA may be isolated from the reaction mass using a suitable solvent, such as acetone.

Alternatively, the organic salts of formula IVA may be used directly, without isolation, in subsequent synthetic steps, for example in steps involving converting the organic salt IVA to valsartan or salts thereof.

In an embodiment, A is oxalic acid. Suitably, a stoichiometric quantity of oxalic acid is added to the compound of formula (IV) to obtain the desired oxalate salt (IVB). The organic acid salt of formula (IVB) may then be isolated and dried by conventional methods.

According to another aspect of the present invention; there is provided a process for the preparation of valsartan (I) or a salt thereof comprising converting a compound of formula (IVA) to valsartan or the salt thereof,

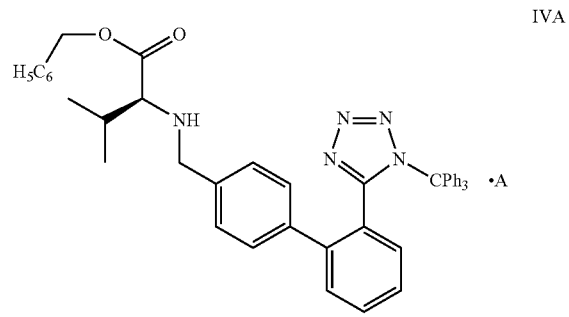

wherein A is an organic carboxylic acid.

In an embodiment, the organic acid is oxalic acid, acetic acid, formic acid, malic acid, maleic acid, malonic acid, succinic acid, fumaric acid, phthalic acid, terephthalic acid, citric acid, tartaric acid, methane sulfonic acid, ethane sulfonic acid, p-toluene sulfonic acid, trifluoroacetic acid or ascorbic acid. Preferably, A is oxalic acid.

In an embodiment, the conversion of the compound (IVA) comprises acylating the compound of formula (IVA) with a suitable acylating agent, for example valeryl halide of formula (V)

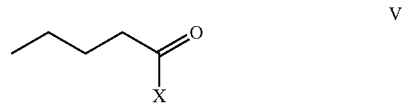

wherein X is halide, in the presence of a base and an organic solvent to obtain a compound of formula (VI)

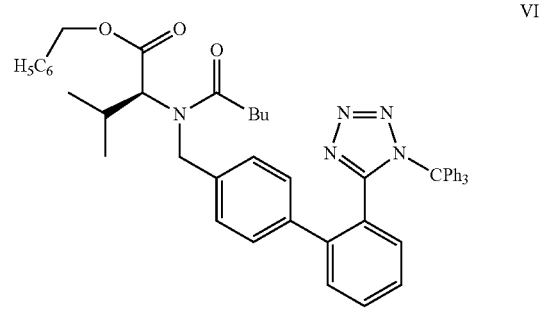

In an embodiment, the valeryl halide is valeryl chloride or valeryl bromide, preferably valeryl chloride.

The organic solvent may be selected from the group consisting of ethylene chloride, chloroform, methylene chloride, ethyl acetate, and toluene. In a preferred embodiment, the solvent used is toluene.

Bases for use in the acylation process may be selected from inorganic bases such as alkali metal carbonates, alkali metal hydroxides, alkali metal alkoxides or organic bases such as tertiary amines, for example triethylamine. In a preferred embodiment, the inorganic base used is diisopropyl ethyl amine.

The reaction time and temperature may vary depending upon the solvent and base used.

The conversion may further comprise detritylating the compound of formula (VI) to obtain benzyl valsartan of formula (VII).

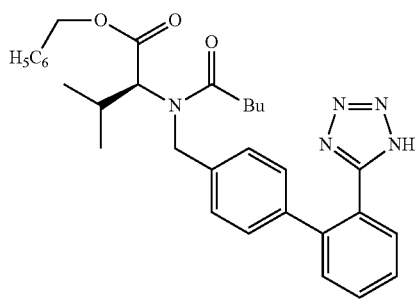

VII

The detritylation step may be carried out using acids such as sulphuric acid, para toluene sulphonic acid, methane sulphonic acid, oxalic acid and hydrochloric acid. The acid may be present in a solvent such as an alcohol, for example methanol, or a ketone, for example acetone. The solvent may be present in pure form or in combination with water, for example acetone in water.

The conversion may further comprise debenzylating the compound of formula (VII) to obtain valsartan (I); and, if required converting valsartan base (I) to a pharmaceutically acceptable salt thereof.

The debenzylation may be carried out in the presence of a noble metal catalyst and hydrogen gas, a phase transfer hydrogenation, or other deprotecting reagents. Other deprotecting agents include mineral acids, strong acids, Lewis acids, aqueous mineral bases. The deprotecting agents may be present in a suitable solvent.

Preferably, the debenzylation is carried out in the presence of a noble metal catalyst and hydrogen gas. The catalyst may be selected from the group consisting of palladium, palladium hydroxide, palladium on activated carbon, palladium on alumina, platinum, platinum on activated carbon and Raney nickel. The solvent used is preferably selected from an alkyl acetate such as ethyl acetate, a lower alkylamine, an alcohol, an aliphatic hydrocarbon, an aromatic hydrocarbon, a heterocycle, a dialkylether, an acid, a mixture of water and water miscible solvents, ionic liquids, halogenated solvents and mixtures thereof.

The compound of formula (IVA) may be prepared by a process as defined above. For example, the preparation of the compound of formula IVA may comprise:
a) reacting L-valine benzyl ester of formula (II) with 4-(bromomethyl-biphenyl-3-yl)-1-(triphenyl methyl)tetrazole of formula (III) to obtain N-[(2'-(1-triphenyl methyl tetrazole-5-yl)biphenyl]-4-yl]methyl]-L-valine benzyl ester of formula (IV);
b) reacting N-[(2'-(1-triphenyl methyl tetrazole-5-yl)biphenyl]-4-yl]methyl]-L-valine benzyl ester of formula (IV) with organic acid to obtain compound of formula (IVA)

In an embodiment, the present invention provides a process for the synthesis of the valsartan intermediate N-[(2'-(1-triphenyl methyl tetrazole-5-yl)biphenyl]-4-yl]methyl]-L-valine benzyl ester as an oxalate salt of formula (IVB).

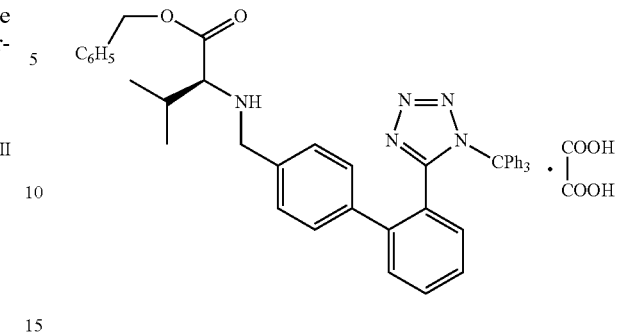

IVB

According to another aspect of the present invention, there is provided valsartan or a salt thereof prepared according to a process defined above. The valsartan prepared according to the process described above may be in any polymorphic form, including amorphous and crystalline forms. It may also be in the form of a hydrate or solvate.

According to another aspect of the present invention, there is provided the use of valsartan or a salt thereof prepared according to a process defined above in medicine.

According to another aspect of the present invention, there is provided the use of valsartan or a salt thereof prepared according to a process defined above in treating hypertension, diabetes related hypertension, heart attack, post myocardial infarction and lung cancer.

The present invention also provides a method of treating a disease state prevented, ameliorated or eliminated by the administration of an angiotensin II receptor antagonist in a patient in need of such treatment, which method comprises administering to the patient a therapeutically effective amount of valsartan, or a pharmaceutically acceptable salt thereof, prepared according to the present invention, substantially as hereinbefore described.

DETAILED DESCRIPTION OF THE INVENTION

The present invention describes a more practical, economical and efficient synthesis for the preparation of pure valsartan. This process is particularly advantageous in comparison with known methods because the reaction is carried out by isolating the intermediates in the form of organic acid addition salts, thus reducing the impurities formed and increasing yield and purity of the product. The processes of the present invention eliminate the risk of handling hazardous chemicals, reduce cost associated reaction time, thus making the processes more economical and industrially viable.

In an embodiment of the present invention there is provided a method of synthesizing an organic salt of formula (IVA) of the intermediate N-[(2'-(1-triphenyl methyl tetrazole-5-yl) biphenyl]-4-yl]methyl]-L-valine benzyl ester of formula (IV), which comprises a first step a):
a) reacting L-valine benzyl ester of formula (II) with 4-(bromomethyl-biphenyl-3-yl)-1-(triphenyl methyl)tetrazole of formula (III) in the presence of an organic solvent using base to obtain N-[(2'-(1-triphenyl methyl tetrazole-5-yl) biphenyl]-4-yl]methyl]-L-valine benzyl ester of formula (IV) as shown in scheme below;

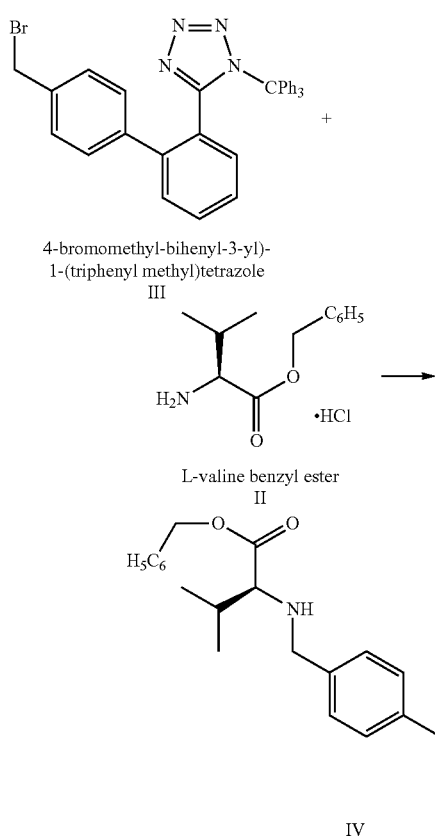

4-bromomethyl-bihenyl-3-yl)-
1-(triphenyl methyl)tetrazole
III

L-valine benzyl ester
II

IV b) reacting N-[(2'-(1-triphenyl methyl tetrazole-5-yl)biphenyl]-4-yl]methyl]-L-valine benzyl ester of formula (IV) with an organic acid to obtain a compound of formula (IVA).

The term organic acid as used herein refers to an organic compound with a —COOH moiety attached to it. The organic acid may be selected from oxalic acid, acetic acid, formic acid, malic acid, maleic acid, malonic acid, succinic acid, fumaric acid, phthalic acid, terephthalic acid, citric acid, tartaric acid, methane sulfonic acid, ethane sulfonic acid, p-toluene sulfonic acid, trifluoroacetic acid, ascorbic acid and the like.

In a preferred embodiment, the organic salt is isolated as the oxalate salt of formula (IVB).

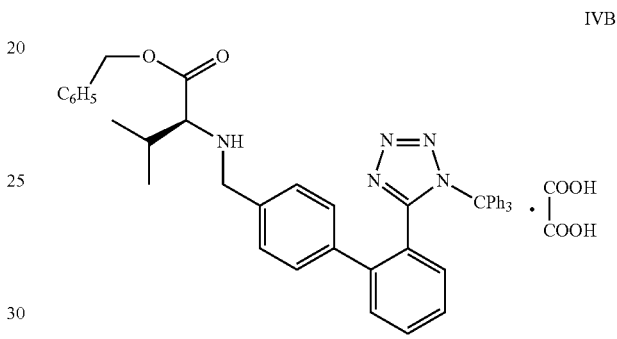

IVB

Various solvents well known to a person skilled in the art can be used. These include but are not restricted to dimethylformamide, dimethyl acetamide, dimethylsulfoxide, acetonitrile, xylene, toluene, a halogenated hydrocarbon such as methylenedichloride, ethylenedichloride or chloroform, an alcohol such as methanol, ethanol, n-propanol, isopropanol, n-butanol, isobutanol, tert-butanol, n-Amyl alcohol, isoamyl alcohol or tertamyl alcohol or mixtures thereof. In one embodiment, the solvent used is acetonitrile.

The bases used are selected from organic bases inorganic bases or mixtures thereof, more preferably sodium hydroxide, potassium hydroxide, calcium hydroxide, magnesium hydroxide, sodium bicarbonate, potassium bicarbonate, sodium carbonate, potassium carbonate, cesium carbonate, sodium methoxide, potassium methoxide, sodium ethoxide, potassium ethoxide, potassium tert-butoxide, ammonia, triethyl amine, pyridine and the like and most preferably sodium carbonate and potassium carbonate.

The reaction is preferably carried out at a temperature in the range from about 20 to about 80° C., more preferably from about 40 to about 80° C., still more preferably in the temperature range from about 60 to about 80° C.

The method of synthesizing an organic salt of formula (IVA) of the intermediate N-[(2'-(1-triphenyl methyl tetrazole-5-yl)biphenyl]-4-yl]methyl]-valine benzyl ester of formula (IV), further comprises a second step b):

A stoichiometric quantity of oxalic acid may be added to the intermediate of formula (IV) to obtain the desired oxalate salt (IVB). The solvent may be selected from the group consisting of water, methanol, ethanol, propanol, isopropanol, tert-butanol, ethyl acetate, acetone, toluene, n-hexane, o-xylene, n-heptane, methylenedichloride, ethylenedichloride, acetonitrile, dimethylformamide, dimethylsulfoxide or mixtures thereof, more preferably water, acetone, toluene, o-xylene or mixtures thereof. The organic acid salt of formula (IVB) may then be isolated and dried by conventional methods.

The organic salts may be easily isolated from the reaction mixture using solvents that are less hazardous than those used in the prior art. In an embodiment, the the use of hexane in the isolation of an oxalate salt is avoided. Thus, both purification steps and solvents are greatly reduced. The isolated intermediate (IVB) has about 96% HPLC purity which means that the subsequent steps may be carried out without any difficulty.

It has been found very surprisingly that the organic salt formed is highly pure and easily crystallizable. The reaction to form the organic salt proceeds at mild acidic conditions as compared to the highly acidic media of pH 1 in the reaction to form the hydrochloride salt of the intermediate (IV), as reported in WO '1534. Hence, the reaction is controllable on the laboratory scale as well as on the industrial scale. Also, organic carboxylic acids are much weaker in acidic strength as compared to hydrochloric acid and hence the risk of detritylation during the formation of organic acid salts is reduced. This forms another aspect of the present invention.

In another embodiment of the present invention, there is provided a process for preparing valsartan (I) or a salt thereof comprising a first step a):

a) acylating a salt of formula (IVB) with valeryl halide of formula (V) as shown in the scheme below, wherein X is a halide

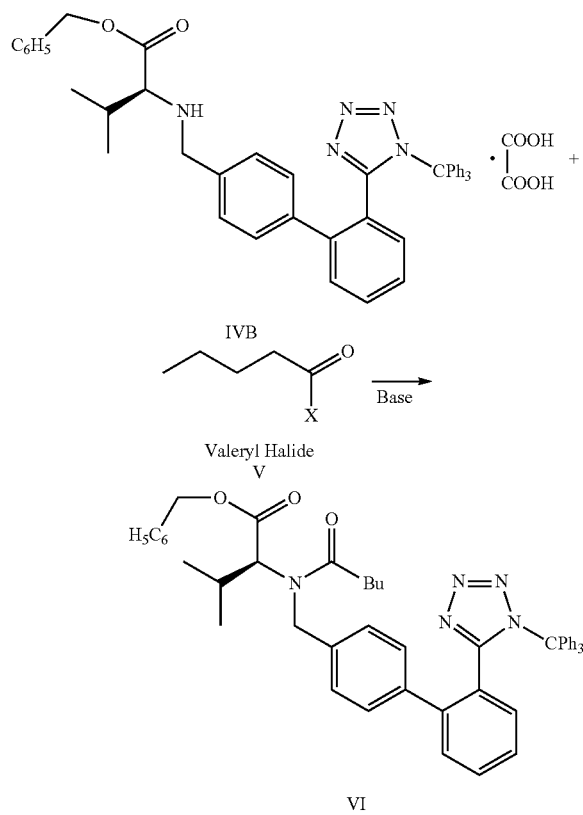

The acylation of the intermediate of formula (IVB) may be carried out in an organic solvent and in the presence of an organic base. Various acylating agents which are commonly known to one skilled in the art may be used. These include but are not restricted to valeryl chloride and valeryl bromide. In an embodiment, the acylating agent used is valeryl chloride (VA).

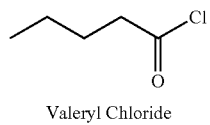

Valeryl Chloride

The solvent may be selected from the group consisting of ethylene chloride, chloroform, methylene chloride, ethyl acetate, and toluene. In a preferred embodiment, the solvent used is toluene.

Bases for use in the acylation process according to the present invention may be selected from inorganic bases such as alkali metal carbonates, alkali metal hydroxides, alkali metal alkoxides or organic bases such as tertiary amines. In a preferred embodiment, the inorganic base used is diisopropyl ethyl amine.

The reaction time and temperature may vary depending upon the solvent and reagent used.

The process for preparing valsartan (I) or salt thereof may further comprise a second step b):

b) detritylating trityl benzyl valsartan of formula (VI) to benzyl valsartan of formula (VII).

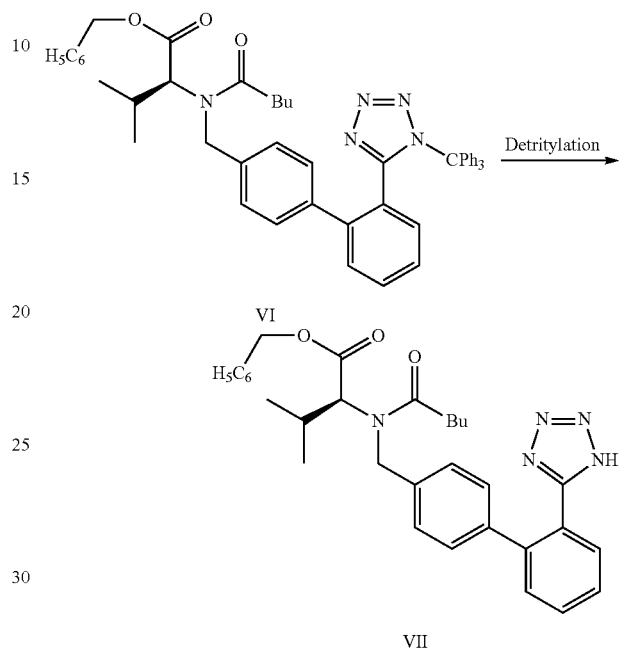

The detritylation step may be carried out by using acids such as sulphuric acid, para toluene sulphonic acid, methane sulphonic acid and hydrochloric acid in a solvent such as alcohols or ketones, as such or in combination with water.

The process for preparing valsartan (I) or salt thereof may further comprise a third step c):

c) debenzylating, benzyl valsartan of formula (VII) to valsartan of Formula (I).

Debenzylation (also known as hydrogenolysis) of the compound of formula (VII) to obtain valsartan base may be carried out in the presence of a noble metal catalyst and hydrogen gas or using a phase transfer hydrogenation or other deprotecting reagents such as mineral acids, strong acids, Lewis acids, aqueous mineral bases in a suitable solvent.

A preferred method for deprotection is catalytic reduction using catalysts such as palladium, palladium hydroxide, palladium on activated carbon, palladium on alumina, platinum, platinum on activated carbon and Raney nickel. The solvent used is preferably selected from an alkyl acetate, a lower alkylamine, an alcohol, an aliphatic hydrocarbon, an aromatic hydrocarbon, a heterocycle, a dialkylether, an acid, a mixture of water and water miscible solvents, ionic liquids, halogenated solvents and mixtures thereof.

The process for preparing valsartan (I) or salt thereof may further comprise a fourth step d):

d) converting valsartan base to a pharmaceutically acceptable salt thereof.

The present invention also provides a method of treating a disease state prevented, ameliorated or eliminated by the administration of an angiotensin II receptor antagonist in a patient in need of such treatment, which method comprises administering to the patient a therapeutically effective amount of valsartan, or a pharmaceutically acceptable salt thereof, prepared according to the present invention, substantially as hereinbefore described.

The invention is explained in more detail in the following working examples. The examples, which illustrate improvement in the method according to the invention, have a purely illustrative character and do not limit the extent of the invention, in any respect.

EXAMPLE 1

Preparation of N-[(2'-{1-triphenylmethyl}-tetrazole-5-yl)biphenyl-4-yl)methyl]-L-valine benzyl ester oxalate Example 1 (i)

100 gms of potassium carbonate was added to a mixture of 500 ml of acetonitrile, 50 gms of L-valine benzyl ester hydrochloride and 130 gms of 5-(4-(bromomethyl) biphenyl-2-yl)-1-(triphenylmethyl)tetrazole. The contents were refluxed at a temperature of 75-78° C. for about 2-3 hours. After the completion of the reaction, the insolubles were filtered off. To this clear filtrate, was added 25 gms of oxalic acid under stirring and the contents were cooled to 0-5° C. The solids were filtered and washed with 100 ml acetonitrile. The resulting wet cake was slurried in 50 ml purified water at ambient temperature. To the slurry was added about 500 ml of acetone and the contents were refluxed at 52-54° C. for 30 minutes, cooled to 25-30° C., filtered and washed with 75 ml acetone, dried under vacuum at 45-50° C. to afford 140 gms of the title compound having 93-96% purity which was used without further purification.

Example 1 (ii)

200 gms of potassium carbonate was added to 1000 ml of acetonitrile, 100.0 gms of L-valine benzyl ester hydrochloride and 260 gms of 5-(4-(bromomethyl)biphenyl-2-yl)-1-(triphenylmethyl)tetrazole. The contents were refluxed at a temperature of 75-78° C. for about 2-3 hours. After the completion of the reaction, the insoluble were filtered off. The solvent was removed by distillation to residue and was stirred with 1.0 lt of acetone and 50.0 gms of oxalic acid. The contents were cooled to 0-5° C. The solids were filtered and washed with 200.0 ml acetone. The resulting wet cake was slurried in 100 ml purified water at ambient temperature. To the slurry was added about 1 lt of acetone and the contents were refluxed at 52-54° C. for 30 minutes, cooled to 25-30° C., filtered and washed with 150 ml acetone, dried under vacuum at 45-50° C. to yield 270 gms of the title compound having 93-96% purity which was used as such without purification for the subsequent step.

Example 1 (iii)

50 gms of potassium carbonate was added to 250 ml of acetonitrile, 25 gms of L-valine benzyl ester hydrochloride and 65 gms of 5-(4-(bromomethyl)biphenyl-2-yl)-1-(triphenylmethyl)tetrazole. The contents were refluxed at a temperature of 75-78° C. for about 2-3 hours. After the completion of the reaction, the insolubles were removed by filteration. The solvent was removed completely by distillation to residue and was added 250 ml of ethyl acetate and 12.5 gms of oxalic acid under stirring. The contents were cooled to 0-5° C. The solids were filtered and washed with 50 ml ethyl acetate. The resulting wet cake was slurried in 25 ml purified water at ambient temperature. To the water slurry, was added about 250 ml acetone and the contents were refluxed for 30 minutes, cooled to 25-30° C., filtered and washed with 40 ml acetone, dried under vacuum at 45-50° C. to afford 68 gms of the title compound having 93-96% purity which was used as the starting material for the subsequent step.

Example 1 (iv)

250 gms of potassium carbonate was added to 1250 ml of acetonitrile, 125 gms of L-valine benzyl ester hydrochloride and 325 gms of 5-(4-(bromomethyl)biphenyl-2-yl)-1-(triphenylmethyl)tetrazole. The contents were refluxed at a temperature of 75-78° C. for about 2-3 hours. After the completion of the reaction, the insolubles were filtered off. Acetonitrile was distilled off completely to residue and 1250 ml of toluene was added together with 62.5 gms of oxalic acid under stirring. The contents were cooled to 0-5° C. The solids were filtered and washed with 250 ml toluene. The resulting wet cake was slurried in 125 ml purified water at ambient temperature. To the slurry was added, about 1250 ml of acetone and the contents were refluxed at 52-54° C. for 30 minutes, cooled to 25-30° C., filtered and washed with 150 ml acetone, dried under vacuum at 45-50° C. to afford 330 gms of the title compound having 93-96% purity which was used such without further purification.

EXAMPLE 2

Trityl Benzyl Valsartan

Example 2 (i)

To 50 gms of N-[(2'-{1-triphenylmethyl}-tetrazole-5-yl)biphenyl-4-yl)methyl]-L-valine benzyl ester oxalate was added 250 ml toluene and 25 ml diisopropyl ethyl amine. The resultant mixture was washed with 300 ml purified water. The organic phase was separated and dried over anhydrous sodium sulphate. The clear solution was cooled to 15-20° C. and 25 ml of N,N diisopropyl ethyl amine and about 12 gms of valeryl chloride were slowly added at this temperature under nitrogen. The contents were stirred for 1 hour. After completion of reaction, the reaction mass was washed with 300 ml purified water followed by 250 ml of 7% sodium bicarbonate solution and 50 ml water. The organic layer was separated and dried over anhydrous sodium sulphate and concentrated to yield about 50-55 gms of title compound having a purity of about 95%.

Example 2 (ii)

To 100 gms of N-[(2'-{1-triphenylmethyl}-tetrazole-5-yl)biphenyl-4-yl)methyl]-L-valine benzyl ester oxalate was added 500 ml toluene and 50 ml triethyl amine. The resultant mixture was washed with 500 ml purified water. The organic phase was separated and dried over anhydrous sodium sulphate. The clear solution was cooled to 15-20° C. Then 50 ml of triethyl amine and 50 gms of valeryl chloride were added slowly maintaining temperature at 15-20° C. under nitrogen. The contents were stirred for 1 hour. After completion of reaction, the reaction mass was washed with 50.0 ml purified water followed by 500 ml of saturated sodium bicarbonate solution and 100 ml water. The organic layer was separated and dried over anhydrous sodium sulphate and concentrated to yield 95-100 gms of trityl benzyl valsartan.

EXAMPLE 3

Benzyl Valsartan

Example 3(i)

100 gms of trityl benzyl valsartan obtained in examples 2(i) or 2(ii) was dissolved in 500 ml of methanol and acidified to about pH 2.0 by using hydrochloric acid. The contents were stirred at 25-30° C. for 1 hour. After completion of reaction, the contents were cooled to 5° C. and stirred for 30 minutes. Insolubles were filtered. The pH of the clear filtrate was adjusted to 7.5 by using liquor ammonia followed by distillation under vacuum by removing methanol completely. The residue obtained was dissolved in about 800.0 ml of ethyl acetate and washed with water. The pH of the organic layer adjusted to 5.5-6.0 using acetic acid. The reaction mass was washed with 500 ml of 10% sodium chloride solution, followed by 100 ml water. The ethyl acetate layer was separated and dried over anhydrous sodium sulphate.

Example 3(ii)

50 gms of trityl benzyl valsartan obtained in examples 2(i) or 2(ii) was dissolved in 250 ml of methanol. To the solution was added 20 gms of para toluene sulphonic acid. The contents were stirred at 25-30° C. for 1 hour. Contents were cooled to 5° C. after completion of reaction and stirred for 30 minutes. The unwanted solids were filtered. The pH of the clear filtrate was adjusted to 7.5 by using liquor ammonia followed by distillation under vacuum to obtain a residue by removing methanol completely. The residue was dissolved in about 500 ml of ethyl acetate and washed with water. The pH of the reaction mass was adjusted to 5.5-6.0 using dilute acetic acid. The reaction mass was washed with 300 ml of 10% sodium chloride solution, followed by 100 ml water. The ethyl acetate layer was separated and dried over anhydrous sodium sulphate.

Example 3(iii)

200 gms of trityl benzyl valsartan obtained in example 2 was dissolved in 1000 ml of methanol followed by 64 gms of oxalic acid. The contents were stirred at 60-65° C. for 1 hour. After completion of reaction, the contents were cooled to 5° C. and stirred for 30 minutes. Insoluble were removed by filtration. The pH of the clear filtrate was adjusted to 7.5 by using liquor ammonia and distilled completely under vacuum to remove methanol. The residue obtained was dissolved in about 1500 ml of ethyl acetate and washed with water. The pH was adjusted to 5.5-6.0 using dilute acetic acid. The reaction mass was washed with 1000 ml of 10% sodium chloride solution, followed by 100 ml water. The ethyl acetate layer was separated and dried over anhydrous sodium sulphate.

Example 3(iv)

100 gms of trityl benzyl valsartan obtained in example 2(i) or 2(ii) was dissolved in 600 ml of acetone and acidified by using dilute sulphuric acid (22 ml in 130 ml purified water). The contents were stirred at 25-30° C. for 8 hours. After completion of reaction, 500 ml purified water was added to the reaction mass and the product extracted in 800 ml ethyl acetate. The pH of the organic layer was adjusted to about 7.5 by using liquor ammonia and washed with purified water. The organic layer was separated and adjusted to pH 5.5-6.0 using acetic acid. The reaction mass was washed with 500 ml of 10% sodium chloride solution followed by 100 ml water. The ethyl acetate layer was separated and dried over anhydrous sodium sulphate.

EXAMPLE 4

(i) Preparation of Valsartan 5.0 gms of 10% dry palladium on carbon was charged to the dried ethyl acetate layer obtained in example 3 (i) and the contents were subjected to hydrogen bubbling over a period of 8-10 hours at 25-30° C. After completion of reaction, the catalyst was removed by filtration. The pH of the clear filtrate was adjusted to 6.5 using liquor ammonia. About 500 ml purified water was added to the reaction mass and stirred for 15 minutes. The resulting mixture was transferred to a separating funnel and the phases separated. The aqueous layer was firsts washed with 1.50 ml ethyl acetate followed by 150 ml tertiary butyl methyl ether. The pH of aqueous layer was adjusted to 3.0 to 4.0 using dilute sulphuric acid or acetic acid and extracted with 500 ml ethyl acetate. The ethyl acetate layers were combined together and washed with 500 ml 10% sodium chloride solution followed by 100 ml water. The organic phase was dried over anhydrous sodium sulphate and concentrated, under vacuum to afford a residue. About 100 ml ethyl acetate was added to the residue and the mixture was stirred for 30 minutes at ambient temperature. The suspension was gradually stirred for 6 hours after the addition of 800 ml n-heptane. The crude solid was separated by filtration, washed with 200.0 ml n-heptane and dried under vacuum at 50-55° C. to give about 45 gms of valsartan.

(ii) Preparation of Valsartan 10 gms of 10% dry palladium on carbon was charged to the dried ethyl acetate layer obtained in example 3 (iii) and the contents were subjected to hydrogen bubbling over a period of 8-10 hours at 25-30° C. After completion of reaction, the catalyst was removed by filtration. The pH of clear filtrate was adjusted to 6.5 using liquor ammonia. About 100 ml purified water was charged to the reaction mass and stirred for 15 minutes. The resulting mixture was transferred to a separating funnel and the phases separated. The aqueous layer was first washed with 300 ml ethyl acetate followed by 300 ml tertiary butyl methyl ether. The pH of aqueous layer was adjusted to 3.0 to 4.0 using dilute sulphuric acid or acetic acid and extracted with 500 ml ethyl acetate twice. The ethyl acetate layers were combined together and washed with 1000 ml 10% sodium chloride solution followed by 2×100 ml water. The organic phase was dried over anhydrous sodium sulphate and concentrated under vacuum to a residue. About 200 ml ethyl acetate was added to the residue and the mixture was stirred for 30 minutes at ambient temperature. The suspension was charged with 1500 ml diisopropyl ether and gradually stirred for 6 hours. The crude solid valsartan was isolated by filtration, washed with 400.0 ml diisopropyl ether and dried under vacuum at 50-55° C. Yield—90-95 gms.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the examples are therefore intended to be embraced therein.

The invention claimed is:

1. A process for preparing a compound of formula (IVA)

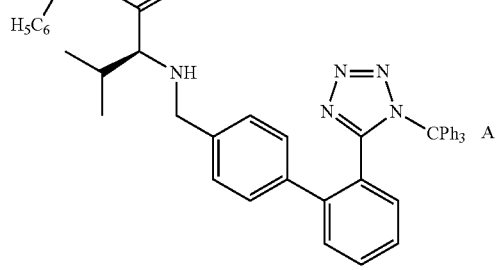

wherein A represents an organic carboxylic acid, which process comprises reacting N-[(2'-(1-triphenyl methyl tetrazole- 5-yl)biphenyl]-4-yl]methyl]-L-valine benzyl ester of formula (IV) with an organic carboxylic acid to obtain the compound of formula (IVA)

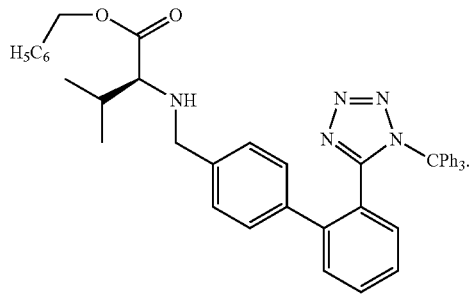

2. The process according to claim 1, wherein the step of converting IV to IVA is carried out in the presence of a solvent selected from the group consisting of water, methanol, ethanol, propanol, isopropanol, cert-butanol, ethyl acetate, acetone, toluene, n-hexane, o-xylene, n-heptane, methylenedichloride, ethylenedichloride, acetonitrile, dimethylformamide, dimethylsulfoxide or mixtures thereof, preferably water, acetone, toluene, o-xylene or mixtures thereof.

3. The process according to claim 1, wherein the compound of formula IV is prepared by reacting L-valine benzyl ester of formula (II)

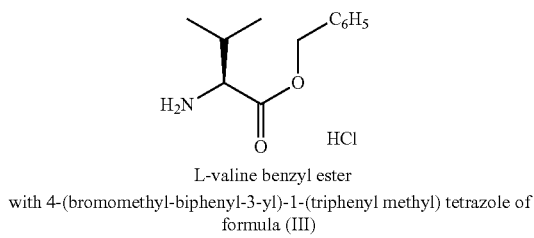

L-valine benzyl ester
with 4-(bromomethyl-biphenyl-3-yl)-1-(triphenyl methyl) tetrazole of formula (III)

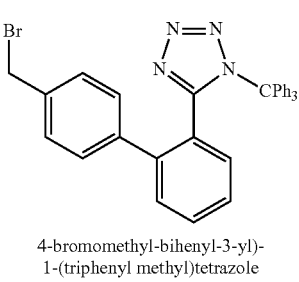

4-bromomethyl-bihenyl-3-yl)-
1-(triphenyl methyl)tetrazole to obtain the compound of formula (IV).

4. The process according to claim 1, wherein the organic salt of formula IVA is isolated from the reaction mass, preferably the isolation is carried out in the absence of hexane.

5. The process according to claim 1, wherein the organic salt of formula IVA is used directly, without isolation, in subsequent synthetic steps, and the subsequent synthetic steps comprise converting the organic salt IVA to valsartan or salts thereof.

6. The process according to claim 1, wherein A is oxalic acid, and preferably a stoichiometric quantity of oxalic acid is added to the compound of formula (IV) to obtain the desired oxalate salt.

7. A process for the preparation of valsartan (I) or a salt thereof comprising:
preparing a compound of formula (IVA)

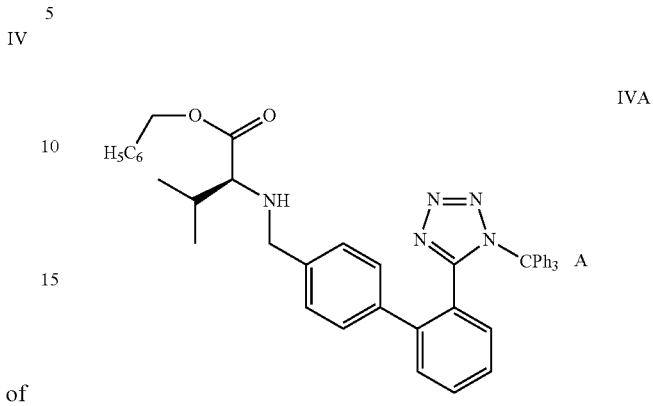

wherein A represents an organic carboxylic acid, which process comprises reacting N-[(2'-(1-triphenyl methyl tetrazole-5-yl)biphenyl]-4-yl]methyl]-L-valine benzyl ester of formula (IV) with an organic carboxylic acid to obtain the compound of formula (IVA)

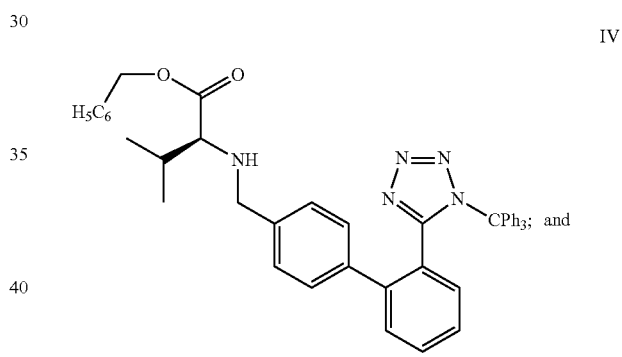

converting the compound of formula (IVA) to valsartan or the salt thereof, wherein A is oxalic acid.

8. The process according to claim 7, wherein the conversion of the compound (IVA) comprises acylating the compound of formula (IVA) with a suitable acylating agent, in the presence of a base and an organic solvent to obtain a compound of formula (VI)

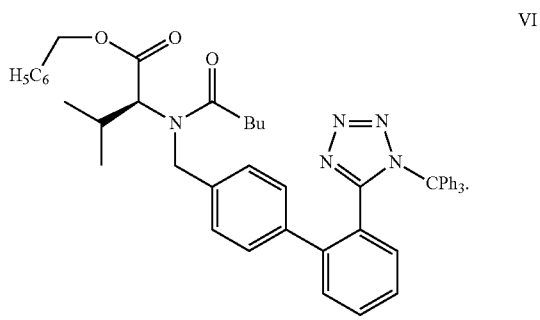

9. The process according to claim 8, wherein the acylating agent is a valeryl halide of formula (V)

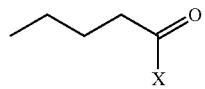

V wherein X is halide, preferably the valeryl halide is valeryl chloride or valeryl bromide, more preferably the valeryl halide is valeryl chloride.

10. The process according to claim 8, wherein the conversion further comprises detritylating the compound of formula (VI) to obtain benzyl valsartan of formula (VII), preferably the detritylation step is carried out using an acid selected from sulphuric acid, para toluene sulphonic acid, methane sulphonic acid, oxalic acid and hydrochloric acid

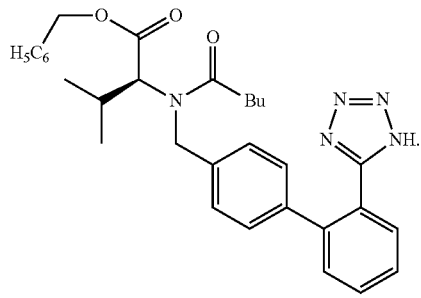

VII

11. The process according to claim 10, wherein the conversion further comprises debenzylating the compound of formula (VII) to obtain valsartan (I); and, if required converting valsartan base (I) to a pharmaceutically acceptable salt thereof, preferably the debenzylation is carried out in the presence of a noble metal catalyst and hydrogen gas, a phase transfer hydrogenation, or other deprotecting reagents.

\* \* \* \* \*